United States Patent [19]

Aalbers et al.

[11] 4,188,311

[45] Feb. 12, 1980

[54] DETERGENT COMPOSITIONS CONTAINING ETHER SULFATES

[75] Inventors: Johan G. Aalbers; Nicolaas I. Van Paassen, both of Bodegraven, Netherlands

[73] Assignee: Chem-Y, Fabriek Van Chemische Produkten B.V., Bodegraven, Netherlands

[21] Appl. No.: 707,092

[22] Filed: Jul. 20, 1976

[30] Foreign Application Priority Data

Jul. 24, 1975 [GB] United Kingdom ............... 31012/75

[51] Int. Cl.² .............................................. C11D 11/04
[52] U.S. Cl. ..................................... 252/551; 252/532; 252/545; 252/DIG. 1
[58] Field of Search ........... 252/89, 532, 551, DIG. 1; 260/458, 615 B

[56] References Cited

U.S. PATENT DOCUMENTS

| | | | |
|---|---|---|---|
| 2,766,212 | 10/1956 | Grifo | 252/551 |
| 3,372,201 | 3/1968 | Leary et al. | 260/615 |
| 3,393,219 | 7/1968 | Myerly et al. | 260/458 |
| 3,395,170 | 7/1968 | Walts et al. | 260/458 |
| 3,413,331 | 11/1968 | Beiser et al. | 260/458 |
| 3,682,849 | 8/1972 | Smith et al. | 260/615 |
| 3,755,407 | 8/1973 | Wilkes | 260/459 |
| 3,775,349 | 11/1973 | Tuvell et al. | 252/547 |
| 3,786,003 | 1/1974 | Hunter | 252/551 |
| 3,803,238 | 4/1974 | Struve et al. | 260/584 |

OTHER PUBLICATIONS

Gollke et al., "Alkyl Ether Sulfates in Liquid Detergents", Part II, Soap and Chemical Specialties, Mar. 1968, pp. 60, 62, 64, 66, 68, 146 and 148.
Schonfeldt, "Surface Active Ethylene Oxide Adducts, "Copyright 1969, Pergamon Press, N.Y., pp. 45, 46 and 55–62.

*Primary Examiner*—P. E. Willis, Jr.
*Attorney, Agent, or Firm*—Browdy and Neimark

[57] ABSTRACT

Detergent compositions containing ether sulfates are provided, wherein ether sulfates are used of the formula $RO-(C_2H_4O)_nSO_3M$, wherein R is an alkyl group containing about 12 to about 15 carbon atoms or a mixture of such groups, n is a number having an average of 1–5 and M is a cation, said ether sulfate having been prepared by ethoxylating a compound ROH with epoxyethane in a manner known per se with the use of acid catalysis, followed by sulfation. Particular advantages are obtained, if the starting product ROH is an alcohol mixture containing a high percentage of branched chain compounds.

6 Claims, No Drawings

DETERGENT COMPOSITIONS CONTAINING ETHER SULFATES

This invention relates to improved detergent compositions, and more particularly to detergent compositions containing alkyl ether sulfates.

Alkyl ether sulfates are a class of detergents which is already known for many years. They have found a wide-spread use, particularly in the cosmetic field, such as in compositions used for showering and shampoos (vide for example British Pat. No. 874,186), but also in dishwashing compositions, carpet shampoos and laundry compositions (vide for instance U.S. Pat. No. 3,658,727). These ether sulfates can be rendered with the formula $RO-(C_2H_4O)_nSO_3M$, wherein R represents hydrophobic hydrocarbon radical, n is a number having an average value of about 1-10 and M is a cation, usually an alkali metal ion, an ammonium ion or a substituted ammonium ion. Among this group of compounds those wherein R represents one or more alkyl groups having about 10 to about 15 carbon atoms and n has an average value of about 1-5 are of particular interest.

As mentioned hereinabove, these compounds, and of course also their preparation are known already for a very long time. The preparation of the ether sulfates is carried out by ethoxylating the corresponding alcohol ROH, usually with ethylene oxide, whereafter the so obtained compound $RO-(C_2H_4O)_nH$ is sulfated, for example with chlorosulfonic acid or sulfur trioxide.

As is also well known, the ethoxylation reaction with ethylene oxide, which is usually carried out in an alkaline medium, leads to the formation of a mixture of ether alcohols, having a broad range of values for n. In the case of average values for n in the lower part of the indicated range, the product will also contain considerable amounts of unreacted starting alcohol. Accordingly, the sulfated final product will show the same kind of distribution of various individual compounds.

Already in 1960 a paper was published by G. Tischbirek in Deutscher Ausschuss fur Grenzflachenaktive Stoffe (C.I.D.), Band I, (1960), wherein a general study of the ethoxylation reaction with ethylene oxide is described. As appears therefrom a much narrower range of products is obtained, when the usual basic catalyst is replaced with a catalyst of the type of the Lewis acids, the best results being obtained with $SbCl_5$. This information was of general interest, because the ethoxylated alcohols are used as intermediates for a large number of surfactants and other chemical compounds. As far as the inventors are aware, no general conclusions were drawn from this possibility of obtaining a narrower distribution of products. Only for one specific class of surfactants, the poly(oxyethylene) acetic acids some advantage was shown in obtaining products within a narrow ethoxylation range, i.e. mixtures which are free from non-ethoxylated compounds and from compounds containing more than five oxyethylene units, vide British Pat. No. 1.027.481. In that specific case the advantage could be attained of obtaining the final products in crystalline form. According to the examples of that patent the individual compounds and fractions were obtained by fractional distillation of the ethoxylated products, whereafter the proper compounds of fractions were used for the conversion to the acetic acid derivatives. According to U.K. Pat. No. 1.335.091 similar products showing a narrow distribution of the number of oxyethylene units, prepared by acid catalysts, are used for flotation purposes.

Whereas the ethoxylated carboxylic acid derivatives are a rather particular group of compounds which, though used for several purposes in fairly large amounts, still should be considered more or less specialized agents, the most popular kinds of anionic surfactants of the ethoxylated type are the poly(oxyethylene) sulfates and they have been so for many years. The preparation of these ether sulfates through polyether alcohols obtained by acid catalysis has not been disclosed in literature. In actual practice these compounds up till now have always been prepared through polyether alcohols obtained by alkaline catalysis. As mentioned already a particular group of ether sulfates to which this invention specifically relates is formed by compounds derived from alcohols having from about 10 to about 15 carbon atoms, and mixtures thereof. A very well known commercial alcohol which is used for this purpose is technical grade lauryl alcohol from natural sources which contains about 70-75% of normal $C_{12}$ and about 25-30% of normal $C_{14}$ alcohol. Synthetic alcohols having numbers of carbon atoms in about this range have become increasingly popular. Such synthetic alcohol mixtures can be obtained for example through the oxoprocess or through the aluminum chemistry. Depending on the exact mode of synthesis such alcohol mixtures may also contain alcohols having odd numbers of carbon atoms and/or branched chain alcohols. Examples of such commercial products are mixtures of $C_{12}$ and $C_{13}$ alcohols and mixtures of $C_{12}$ up to and inclusive $C_{15}$ alcohols.

For several purposes, and particularly for use in cosmetic detergent compositions and compositions for non-automatic dishwashing, highly important properties are the foaming properties (sudsing power and foam stability), and the viscosity which can be attained by adding common salt. Also the cloud point and clear point are important, particularly if the compositions have to be stored in cold climates.

As regards the foaming properties, the polyether sulfates derived from the usual commercial alcohol mixtures through intermediates obtained by alkaline catalysis are usually prepared with an average of about 2.0 oxyethylene units, because this was considered the optimum.

Surprisingly, it has been found that when starting from usual commercial alcohol product derived from vegetable source which contains about 70% of lauryl and about 30% of myristyl alcohol, and using acid catalysis for the ethoxylation, a value of about 2.0 for n is no longer an optimum, but even constitutes a minimum as regards the foaming properties. The best foaming properties are now obtained for such hydrophobic residues with values of n of about 1 to 1.5 or a little higher, while for values of n higher than about 2.1 to somewhat over about 3 the foaming properties are again better than when n is about 2.0.

As regards viscosity, an adequate viscosity is a highly desired property for diluted detergent solutions for the human body and the hair, because otherwise the detergent solution too easily drips off the skin and hair of the user and cannot be distributed in the proper way over the entire area to be treated. Also for a non-mechanical dishwashing viscous products are desired, a.o. because it is easier to add the desired number of drops to the washing water, when the composition is viscous. The diluted solutions of the commercial alkyl ether sulfates available up till now, especially those with linear alkyl chains, can be made viscous by the addition of common salt, which is commercially advantageous. In this respect, however, the commercial synthetic alcohol mixtures sometimes give problems, because the possibility of thickening them with common salt generally decreases with increasing content of branched chain products. Consequently, some commercial synthetic alcohol mixtures give problems, because aqueous solutions of ether sulfates prepared therefrom cannot be thickened sufficiently to be used in detergents for cosmetic purposes and for non-mechanical dishwashing. In some other cases although a desired viscosity can be attained, the cloud point, and particularly the clear point of the solution is so high that it is unacceptable for commercial use.

Surprisingly, it has now been found that the ether sulfates obtained by ethoxylating a starting alcohol with acid catalysis, and sulfating the obtained ethoxylated product yield aqueous solutions which always can be much more effectively thickened with common salt than the corresponding products obtained through basic catalysis. This phenomenon for which as yet no explanation has been found, makes it possible to use also commercial alcohols which in the classical way yielded ether sulfates which could not be sufficiently thickened in aqueous solution. This means that some further cheap commercial products have become available for being converted to ether sulfates which can be used in detergents for cosmetic purposes and for non-mechanical dishwashing.

Although the present alkyl ether sulfates are especially useful for the above mentioned purposes in view of the above-discussed properties, the special properties now attained do not detract from their other properties and usefulness. Thus, they are suitable for all other purposes for which the usual alkyl ether sulfates were used up till now, such as in laundering compositions. Because their optimum sudsing properties usually are obtained at a somewhat different oxyethylene content than is the case with the usual alkyl ether sulfates, and because anyway the alkylether sulfates used according to the present invention show a much narrower distribution of the oxyethylene content, and particularly contain much less non-oxyethylated alkyl sulfate, they possess the general advantages of purer products, as compared with impurer products.

Accordingly, the present invention provides detergent compositions, wherein ether sulfates of the formula RO—$(C_2H_4O)_nSO_3M$ are used, wherein R is the residue of one or more alkyl groups having about 10 to about 15 carbon atoms, n is a number having an average value of about 1 to about 5 and M is a cation, said alkyl ether sulfate having been prepared by ethoxylating a compound ROH with epoxyethane with the use of acid catalysis, followed by sulfation.

The ether sulfates which are used according to the present invention are prepared—as will be clear from the above—according to reaction steps which are known per se. The starting alcohol for detergents for cosmetic purposes and for non-mechanical dishwashing is preferably a commercial alcohol mixture having an average of somewhat over 12 carbon atoms, but of course also pure alcohols can be used, and also alcohols having somewhat higher or somewhat lower numbers or average numbers of carbon atoms. As is always the case in such products, a higher average oxyethylene content is necessary with increasing length of the hydrophobic alkyl chain. The oxyethylation is carried out in the known way with ethylene oxide and with the use of an acidic catalyst, preferably $SbCl_5$. The ethoxylated product is then sulfated and this sulfation is carried out in the same way as with the ethoxylated product obtained by the classical method with basic catalysis. Thus the sulfation can be carried out advantageously with chlorosulfonic acid or $SO_3$ or oleum. The sulfated product is then neutralized and converted to the desired salt.

The invention will be elucidated hereinafter with some experiments, it being understood, that the invention and its advantages are not limited to the compositions and advantages shown hereinafter.

In these experiments the following commercial alcohol products were used as starting products:

natural alcohol: this is a straight chain alcohol mixture derived from natural sources containing about 70% $C_{12}$ and about 30% $C_{14}$ alcohol.

Dobanol 23: commercial mixture of synthetic alcohols of 12 and 13 carbon atoms.

Dobanol 25: commercial mixture of synthetic alcohols having 12, 13, 14 and 15 carbon atoms.

Lial 125: commercial mixture of synthetic alcohols of 12–15 carbon atoms, having a large content of branched-chain alcohols.

Myristyl: commercial grade of myristyl alcohol.

Foaming Properties

A number of alkylether sulfates were prepared by ethoxylating the starting alcohol using $SbCl_5$ as catalyst, followed by sulfation with chlorosulfonic acid, and neutralization to prepare the sodium salt. The various alkylether sulfates were prepared as usual concentrates having a concentration of 28%. Each concentrate was diluted with water having a German hardness of 15° in an amount of 1 g of concentrate per liter of water. The diluted solutions were subjected to the Ross and Miles test at 37° C. The following results were obtained:

| Starting alcohol | n (average) | Foam height in mm. after | | | | |
|---|---|---|---|---|---|---|
| | | 0 min | 5 min. | 10 min. | 15 min. | 20 min. |
| Myristyl | 1 | 178 | 158 | 153 | 150 | 145 |
| Myristyl | 2 | 153 | 133 | 128 | 123 | 123 |
| Myristyl | 3 | 153 | 133 | 130 | 128 | 125 |
| Natural | 1 | 183 | 160 | 158 | 155 | 153 |
| Natural | 2 | 163 | 148 | 145 | 140 | 138 |
| Natural | 3 | 158 | 138 | 135 | 133 | 130 |
| Lial 125 | 2 | 150 | 140 | 135 | 125 | 120 |

As appears from the above data, the optimum foaming properties are obtained at values of n below 2.

Starting from Lial 125 alkylether sulfates were prepared through acid ($SbCl_5$) and alkaline (NaOH) catalysis, and the concentrates were diluted and subjected to the Ross and Miles test as described hereinabove. The results were as follows:

| n (average) | catalyst | Foam height in mm. after | | | | |
|---|---|---|---|---|---|---|
| | | 0 min. | 5 min. | 10 min. | 15 min. | 20 min. |
| 2 | NaOH | 150 | 140 | 135 | 125 | 120 |
| 3 | NaOH | 160 | 145 | 135 | 120 | 100 |
| 2′5 | $SbCl_5$ | 175 | 155 | 140 | 125 | 100 |

From the above-described natural alcohol two alkylether sulfates were prepared. Product A was prepared by ethoxylating with the usual basic catalysis to a product, wherein n=2, followed by sulfation. Product B was prepared by ethoxylation with SbCl$_5$ as catalyst and with n=1.5, also followed by sulfation. Both products were tested for their foaming properties in a mixture with glycol mono stearate, lanoline and lecithine, which mixtures are usual in detergent compositions for the human body and hair. Both compositions were dissolved in water to an amount of 1 g/l of the ether sulfate. The water had a German hardness of 15°. Both solutions were subjected to the Ross and Miles test at 37° C. The following results were obtained:

| Solution containing | Foam height in mm. after | | | |
|---|---|---|---|---|
| | 0 min. | 5 min. | 10 min. | 15 min. |
| Product A | 95 | 93 | 84 | 80 |
| Product B | 123 | 115 | 113 | 110 |

The above results show that the foaming properties of the product obtained through acid catalysis are superior at a lower oxyethylene content.

THICKENING PROPERTIES

A number of ether sulfates RO(C$_2$H$_4$O)$_2$SO$_3$Na were prepared, starting from various commercial alcohol products. In some experiments the ethoxylation was carried out with NaOH as the catalyst and in some other experiments with SbCl$_5$. The obtained sulfates were diluted with water to a concentration of 7% and then NaCl was added, and the percentage thereof for maximum viscosity, the value of the maximum viscosity, the cloud point and the clear point were determined. As regards the viscosity, it should be remarked that diluted aqueous solutions of ether sulfates possess the general property that their viscosity passes through a maximum on the addition of increasing amounts of common salt. The salt percentage for maximum viscosity, and the value of the maximum viscosity depend on the exact nature of the ether sulfate. The cloud point is the temperature at which the solution turns cloudy on cooling and the clear point is the temperature, at which the cloudy solution on reheating turns clear again. The results were as follows:

| Starting alcohol | Catalyst for ethoxylation | % NaCl added to 7% aqueous solution of ethersulfate for maximum viscosity | Viscosity of obtained solution | Cloud point, °C. | Clear point, °C. |
|---|---|---|---|---|---|
| Dobanol 23 | NaOH | 6.5 | 4200 | −4 | +2 |
| Dobanol 23 | SbCl$_5$ | 5.8 | 19500 | −6 | +1 |
| Dobanol 25 | NaOH | 6 | 8100 | −2 | +10 |
| Dobanol 25 | SbCl$_5$ | 4.5 | 35000 | +2 | +8 |
| Nat | NaOH | 7 | 12500 | −5 | +2 |
| Nat | SbCl$_5$ | 6.75 | 33000 | −3 | +2 |
| Lial 125 | NaOH | 6 | 800 | −4 | 0 |
| Lial 125 | SbCl$_5$ | 4 | 6900 | −7 | 0 |

As appears clearly from the above table, the products prepared with the use of acid catalysis can be thickened much more effectively.

As also appears from the above table, an ether sulfate obtained through alkaline catalysis from alcohol mixtures containing a high content of branched-chain compounds, like the commercial product Lial 125, cannot be used successfully in detergents for cosmetic purposes and non-automatic dishwashing, because it cannot be thickened sufficiently. On the other hand such products have the advantage of a combination of a low cloud point and a low clear point which would make such a composition particularly suitable for cold climates. It appears that the corresponding ether sulfates prepared through acidic catalysis not only can be thickened very well with a small amount of NaCl, but moreover show an extremely low cloud point and a low clear point.

Accordingly, it is a special and preferred aspect of the present invention that a larger spectrum of alcohols is made available which can be used for the preparations of ether sulfates which can be thickened sufficiently for being used in the cosmetic field or for non-automatic dishwashing.

Consequently, according to an especially preferred embodiment the present invention provides alkylether sulfates, derived from alcohols or alcohol mixtures containing a considerable content of branched-chain compounds, for instance 30% or more, by reacting these alcohols with ethylene oxide using acid catalysts, followed by an usual sulfonation.

Although the foregoing experiments have been carried out with certain commercial starting materials and some specific catalysts, it is a matter of course that the invention is not restricted to such materials and catalysts. Thus other alcohols or alcohol mixtures having a carbon content within the above mentioned range, and especially containing a high content of branched-chain compounds can be used as starting products, and any catalyst for the ethoxylation can be used which gives the required narrow product distribution.

What is claimed is:

1. In a detergent composition consisting essentially of a detergent effective amount of detergent product and a detergent adjuvant, the improvement wherein said detergent product is of the formula RO—(C$_2$H$_4$O)$_n$SO$_3$M, wherein R is a mixture of alkyl groups having from about 10 to about 15 carbon atoms and containing at least about 30% of alkyl groups with branched carbon chains, n is a number having an average value of about 1 to about 5 and M is a cation, said detergent product having been prepared by ethoxylating the corresponding compound ROX with ethylene oxide using an acidic catalyst, followed by sulfation and conversion to the desired salt, and further wherein said detergent product and said detergent adjuvant are in aqueous solution and the composition further includes a thickening amount of sodium chloride.

2. A composition in accordance with claim 1 wherein said cation is an alkali metal ion, ammonium ion or a substituted ammonium ion.

3. A composition in accordance with claim 1 wherein said acidic catalyst is SbCl$_5$.

4. A detergent composition comprising a dilute aqueous solution of a compound of the formula RO—(C$_2$-

H$_4$O)$_n$SO$_3$M, wherein R is a mixture of alkyl groups having from about 10 to about 15 carbon atoms containing at least about 30% of alkyl groups with branched carbon chains, n is a number having an average value of about 5 and M is a cation, said compound having been prepared by ethoxylating the corresponding compound ROX with ethylene oxide using an acidic catalyst, followed by sulfation and conversion to the desired salt, said composition further comprising a thickening amount of sodium chloride.

5. A detergent composition in accordance with claim 4 wherein said cation is an alkali metal ion, ammonium ion or a substituted ammonium ion.

6. A detergent composition in accordance with claim 5 wherein said acidic catalyst is SbCl$_5$.